(12) United States Patent
Eder et al.

(10) Patent No.: US 12,290,677 B2
(45) Date of Patent: May 6, 2025

(54) SAFETY CRITICAL ELECTRONIC DEVICE LOCK

(71) Applicant: Cochlear Limited, Macquarie University (AU)

(72) Inventors: Helmut Christian Eder, Macquarie University (AU); Michael Trieu, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 1086 days.

(21) Appl. No.: 17/261,234

(22) PCT Filed: Sep. 6, 2019

(86) PCT No.: PCT/IB2019/057535
§ 371 (c)(1),
(2) Date: Jan. 19, 2021

(87) PCT Pub. No.: WO2020/053725
PCT Pub. Date: Mar. 19, 2020

(65) Prior Publication Data
US 2021/0268265 A1    Sep. 2, 2021

Related U.S. Application Data

(60) Provisional application No. 62/730,166, filed on Sep. 12, 2018.

(51) Int. Cl.
*A61N 1/08* (2006.01)
*A61N 1/02* (2006.01)
(Continued)

(52) U.S. Cl.
CPC .............. *A61N 1/025* (2013.01); *A61N 1/08* (2013.01); *A61N 1/36038* (2017.08);
(Continued)

(58) Field of Classification Search
None
See application file for complete search history.

(56) References Cited

U.S. PATENT DOCUMENTS 5,653,735 A * 8/1997 Chen .................... A61N 1/3622
607/9
6,282,450 B1 * 8/2001 Hartlaub ............. G06F 11/1433
714/E11.135
(Continued)

FOREIGN PATENT DOCUMENTS

CN    105705197 A    6/2016
CN    106132477 A    11/2016

OTHER PUBLICATIONS

Shih-Lien Lu. (1999). Memory Architecture. In Wiley Encyclopedia of Electrical and Electronics Engineering, J.G. Webster (Ed.). https://doi.org/10.1002/047134608X.W1660.*
(Continued)

*Primary Examiner* — Lynsey C Eiseman
*Assistant Examiner* — James Moss
(74) *Attorney, Agent, or Firm* — Edell, Shapiro & Finnan, LLC (57) ABSTRACT

Presented herein are techniques for electronically locking an electronic device in response to detection of a safety critical fault. As used herein, a "safety critical fault" is a fault having a potential to cause harm to an individual using the device. In particular, an electronic device in accordance with certain embodiments presented herein is configured to determine when the electronic device has experienced a safety critical fault. In response, the electronic device automatically restarts itself and, following restart, is automatically forced into a locked mode. The locked mode prevents execution of a run-time program stored in the electronic device.

23 Claims, 6 Drawing Sheets

(51) Int. Cl.
*A61N 1/36* (2006.01)
*G06F 11/07* (2006.01)
*G16H 40/40* (2018.01)

(52) U.S. Cl.
CPC ...... *A61N 1/36142* (2013.01); *G06F 11/0736* (2013.01); *G06F 11/0751* (2013.01); *G16H 40/40* (2018.01); *G06F 2201/81* (2013.01)

(56) References Cited

U.S. PATENT DOCUMENTS

| | | | | |
|---|---|---|---|---|
| 6,635,048 | B1* | 10/2003 | Ullestad | G06F 11/1666 604/890.1 |
| 6,662,049 | B1 | 12/2003 | Miller | |
| 9,446,252 | B2 | 9/2016 | Benson | |
| 2003/0114899 | A1* | 6/2003 | Woods | A61N 1/3787 607/43 |
| 2004/0030323 | A1* | 2/2004 | Ullestad | A61M 5/14276 714/E11.135 |
| 2007/0091687 | A1* | 4/2007 | Armstrong | A61N 1/37264 365/185.29 |
| 2007/0208261 | A1 | 9/2007 | Maniak et al. | |
| 2009/0132061 | A1 | 5/2009 | Stubbs et al. | |
| 2010/0204766 | A1* | 8/2010 | Zdeblick | A61N 1/025 607/119 |
| 2011/0125221 | A1 | 5/2011 | Sieracki et al. | |
| 2012/0290028 | A1 | 11/2012 | Doerr | |
| 2013/0096648 | A1 | 4/2013 | Benson | |
| 2013/0338450 | A1 | 12/2013 | Osorio et al. | |
| 2014/0082607 | A1 | 3/2014 | Bernstein et al. | |
| 2015/0151131 | A1* | 6/2015 | Huelskamp | A61N 1/025 607/59 |
| 2015/0209589 | A1* | 7/2015 | Jenison | A61M 5/14276 607/59 |

OTHER PUBLICATIONS

Gordon Agnew. (1999). Digital Storage. In Wiley Encyclopedia of Electrical and Electronics Engineering, J.G. Webster (Ed.). https://doi.org/10.1002/047134608X.W1631.*

Thomas Schmidt, CRC Generating and Checking, Microchip, https://ww1.microchip.com/downloads/en/AppNotes/00730a.pdf, 2000, viewed on Mar. 6, 2024.*

International Search Report and the Written Opinion, PCT/IB2019/057535, Jan. 7, 2020, 14 pages.

* cited by examiner

SAFETY CRITICAL ELECTRONIC DEVICE LOCK

BACKGROUND

Field of the Invention

The present invention generally relates to techniques for electronically locking a device in response to a safety critical fault.

Related Art

Individuals make use of a variety of electronic devices, such as televisions, computers, mobile computing devices, etc., on a daily basis. A subset of individuals make use of a specific type of electronic device referred to as medical devices. Medical devices are electronic devices that perform one or more medical functions. For example, medical prosthesis/devices having one or more implantable components, generally referred to herein as implantable medical prostheses, have provided a wide range of therapeutic benefits to the device recipients (i.e., individuals in which the component is implanted) over recent decades. In particular, partially or fully-implantable medical prostheses such as auditory prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions for a number of years.

The types of implantable medical prostheses and the ranges of functions performed thereby have increased over the years. For example, many implantable medical prostheses now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical prosthesis.

SUMMARY

In one aspect, a method is provided. The method comprises: determining, with an implantable component of a medical device, that the implantable component has experienced a safety critical fault; automatically restarting the implantable component; and automatically forcing the implantable component into a locked mode following restarting of the implantable component, wherein the locked mode prevents execution of a run-time program stored in the implantable component.

In another aspect, an electronic device is provided. The electronic device comprises: non-volatile memory (NVM) configured to store a run-time program; and at least one processor configured to: execute the run-time program, wherein the execution of the run-time program detects a safety critical fault in operation of the electronic device and intentionally corrupts the NVM; restart the electronic device and initiate a locked mode, wherein the locked mode includes validation of the NVM of the device; determine that the NVM is corrupt; and in response to determination that the NVM is corrupt, prevent re-execution of the run-time program.

In another aspect, one or more non-transitory computer readable storage media encoded with instructions are provided. When the one or more non-transitory computer readable storage media are executed by a processor, the instructions cause the processor to: determine, using data from an integrated diagnostic mechanism of an electronic device, that the electronic device has experienced a safety critical fault; automatically restart the electronic device; determine whether non-volatile memory (NVM) of the electronic device is corrupt; and in response to determining that the NVM is corrupt, indefinitely execute code stored in read-only memory (ROM) of the electronic device.

BRIEF DESCRIPTION OF THE DRAWINGS

Embodiments of the present invention are described herein in conjunction with the accompanying drawings, in which.

DETAILED DESCRIPTION

Presented herein are techniques for electronically locking an electronic device in response to detection of a safety critical fault. As used herein, a "safety critical fault" is a fault having a potential to cause harm to an individual using the device. In particular, an electronic device in accordance with certain embodiments presented herein is configured to determine when the electronic device has experienced a safety critical fault. In response, the electronic device automatically restarts itself and, following restart, is automatically forced into a locked mode. The locked mode prevents execution of a run-time program stored in the electronic device.

Merely for ease of description, the techniques presented herein are primarily described herein with reference to one illustrative electronic device, namely a type of implantable medical prosthesis referred to as a cochlear implant. However, it is to be appreciated that the techniques presented herein may also be used with a variety of other electronic devices that can suffer safety critical faults, such as implantable components of medical prostheses that provide a wide range of therapeutic benefits to recipients. For example, it is to be appreciated that the techniques presented herein may be used with auditory prostheses other than cochlear implants, including acoustic hearing aids, auditory brainstem stimulators, bone conduction devices, middle ear auditory prostheses, direct acoustic stimulators, bimodal auditory prosthesis, bilateral auditory prosthesis, etc., as well as other implantable components, such as implantable pacemakers, spinal cord stimulators, deep brain stimulators, motor cortex stimulators, sacral nerve stimulators, pudendal nerve stimulators, vagus/vagal nerve stimulators, trigeminal nerve stimulators, retinal or other visual prosthesis/stimulators, occipital cortex implants, diaphragm (phrenic) pacers, pain relief stimulators, other neural or neuromuscular stimulators, etc.

Figure 1:
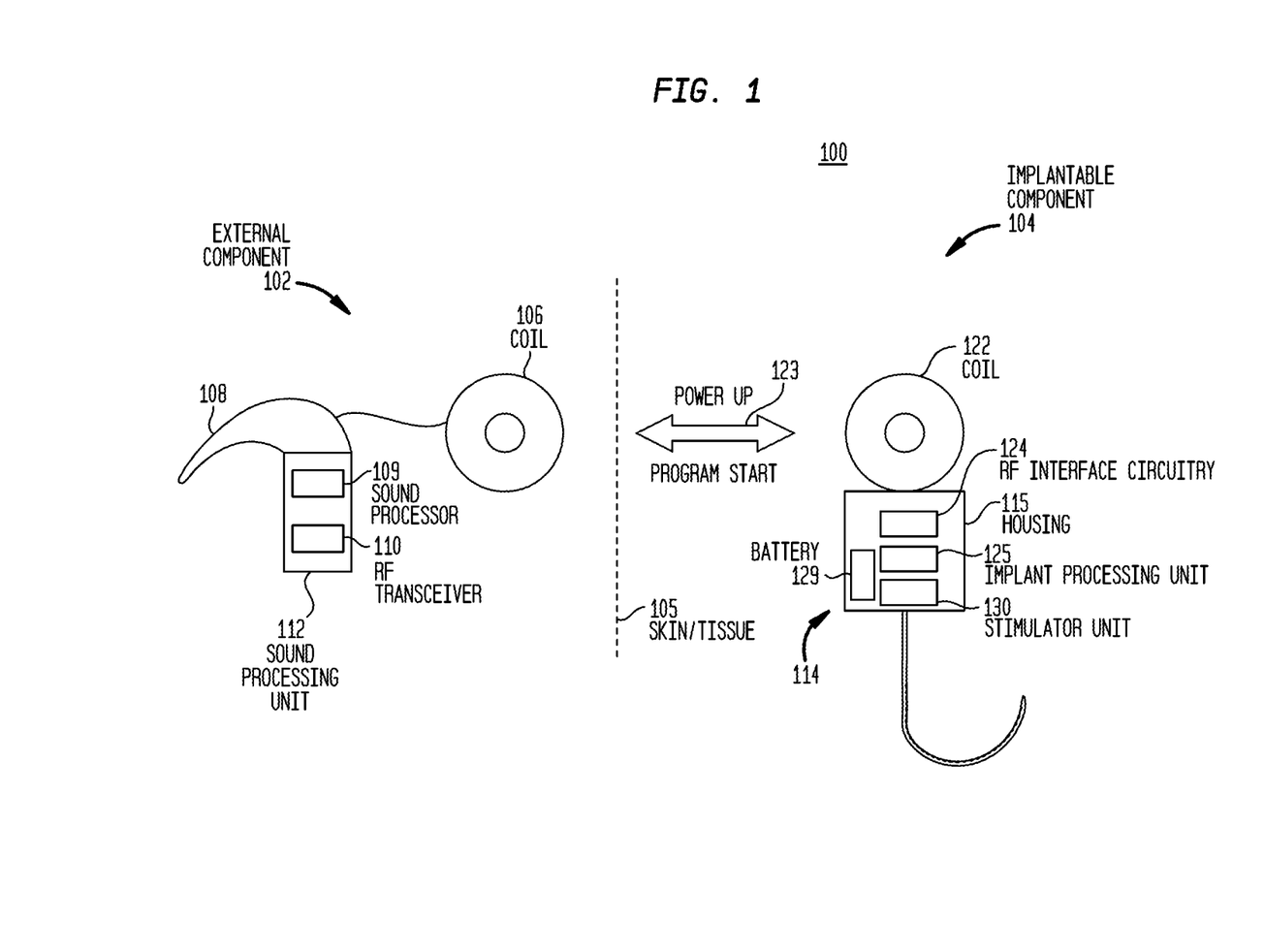
FIG. 1 is a block diagram illustrating a cochlear implant, in accordance with certain embodiments presented herein.

FIG. 1 is a schematic diagram of an exemplary cochlear implant 100 configured to implement aspects of the techniques presented herein. The cochlear implant 100 comprises an external component 102 and an internal/implantable component (implant) 104. The external component 102 is configured to be directly or indirectly attached to the body of the recipient and typically comprises an external coil 106 and, generally, a magnet (not shown in FIG. 1) fixed relative to the external coil 106. The external component 102 also comprises a sound processing unit 112.

The sound processing unit 112 includes one or more sound input devices for receiving sound signals. FIG. 1 illustrates one example sound input device, namely a microphone 108. However, it is to be appreciated that additional microphones and additional types of sound input devices (e.g., telecoils, etc.) may also be included in the sound processing unit 112. The sound processing unit 112 also includes a sound processor 109 and a radio-frequency (RF) transceiver 110.

The implantable component 104 comprises an implant body (main module) 114, a lead region 116, and an intra-cochlear stimulating assembly 118, all configured to be implanted under the skin/tissue (tissue) 105 of the recipient. The implant body 114 generally comprises a hermetically-sealed housing 115 in which RF interface circuitry 124, an implant processing unit 125, a battery 129, and a stimulator unit 130 are disposed. The implant body 114 also includes an internal/implantable coil 122 that is generally external to the housing 115, but which is connected to the RF interface circuitry 124 via a hermetic feedthrough (not shown in FIG. 1).

As noted, stimulating assembly 118 is configured to be at least partially implanted in the recipient's cochlea (not shown in FIG. 1). Stimulating assembly 118 includes a plurality of longitudinally spaced intra-cochlear electrical stimulating contacts (electrodes) 126 that collectively form a contact or electrode array 128 for delivery of electrical stimulation (current) to the recipient's cochlea. Stimulating assembly 118 extends through an opening in the recipient's cochlea (e.g., cochleostomy, the round window, etc.) and has a proximal end connected to stimulator unit 120 via lead region 116 and a hermetic feedthrough (not shown in FIG. 1). Lead region 116 includes a plurality of conductors (wires) that electrically couple the electrodes 126 to the stimulator unit 120.

As noted, the cochlear implant 100 includes the external coil 106 and the implantable coil 122. The coils 106 and 122 are typically wire antenna coils each comprised of multiple turns of electrically insulated single-strand or multi-strand platinum or gold wire. Generally, a magnet is fixed relative to each of the external coil 106 and the implantable coil 122. The magnets fixed relative to the external coil 106 and the implantable coil 122 facilitate the operational alignment of the external coil with the implantable coil. This operational alignment of the coils 106 and 122 enables the external component 102 to transmit data, as well as possibly power, to the implantable component 104 via a closely-coupled wireless link 123 formed between the external coil 106 with the implantable coil 122. In certain examples, the closely-coupled wireless link 123 is a radio frequency (RF) link. However, various other types of energy transfer, such as infrared (IR), electromagnetic, capacitive and inductive transfer, may be used to transfer the power and/or data from an external component to an implantable component and, as such, FIG. 1 illustrates only one example arrangement.

As noted above, sound processing unit 112 includes the sound processor 133 that is configured to convert input audio signals into stimulation control signals for use in stimulating a first ear of a recipient (i.e., the sound processor 133 is configured to perform sound processing on input audio signals received at the sound processing unit 112). Stated differently, the sound processor 133 (e.g., one or more processing elements implementing firmware, software, etc.) is configured to convert the captured input audio signals into stimulation control signals that represent electrical stimulation for delivery to the recipient.

In the embodiment of FIG. 1, the stimulation control signals generated by the sound processor 109 are provided to the RF transceiver 110, which transcutaneously transfers the stimulation control signals (e.g., in an encoded manner) to the implantable component 104 via external coil 106 and implantable coil 122. That is, the stimulation control signals are received at the RF interface circuitry 124 via implantable coil 122 and provided to the stimulator unit 120. The stimulator unit 120 is configured to utilize the stimulation control signals to generate electrical stimulation signals (e.g., current signals) for delivery to the recipient's cochlea via one or more stimulating contacts 126. In this way, cochlear implant 100 electrically stimulates the recipient's auditory nerve cells, bypassing absent or defective hair cells that normally transduce acoustic vibrations into neural activity, in a manner that causes the recipient to perceive one or more components of the input audio signals.

As noted above, the implantable component 104 also includes an implant processing unit 125. In general, the implant processing unit 125 is configured to initiate and control operation of the implantable component 104. In addition, the implantable component 104 is configured to implement diagnostic safety mechanisms for the implantable component and, as described below, electronically "lock" the implantable component when a safety critical fault is detected.

More specifically, the implant processing unit 125 implements one or more diagnostic safety mechanisms that are active while a recipient is using the implantable component. These diagnostic safety mechanisms can be configured to, for example, monitor for short circuit conditions at the implant electronics and/or the electrode array 128, monitor the battery 129 (e.g., monitoring to determine whether a maximum battery voltage threshold has been reached/exceeded, monitoring for a battery overcharge condition, etc.), monitor for faults in a voltage measurement system, monitor for electrical leakage to tissue, monitoring for memory hard errors, etc.

In accordance with certain embodiments presented herein, when these diagnostic safety mechanisms of implant processing unit 125 detect a fault in the operation of the implantable component 104, the implant processing unit 125 is configured to execute a reset of the implantable component to ensure the implantable component immediately ceases operation and is placed in a safe state (i.e., a state in which any potential hazards/dangers to the recipient are remediated). The reset of the implantable component could be achieved in a number of different manners. In one example, the reset disconnects all electrodes from tissue, stops/terminates all processing, and disconnects the internal battery 129 from the other internal circuitry (thereby powering down the implant if no external power is supplied).

Following the reset, the implant processing unit 125 restarts operation and determines the cause of the reset. If the implant processing unit 125 determines that the cause of the reset was a "safety critical fault" (i.e., a fault/condition causing a potentially hazardous situation for the recipient), then the implant processing unit 125 is configured to initiate another reset and cause the implantable component to enter an electronic "locked mode," where only basic, non-hazardous functionality is supported. This functionality may include, for example, allowing interrogation of internal memory of the implantable component and the ability to unlock the implantable component. The unlocking may only be allowed, for example, in a clinic following an assessment by a trained clinician or engineer as to the risk associated with the fault that triggered the safety check. Further details regarding electronically locking of the implantable component 104 are described further below with reference to FIGS. 2 and 3.

Figure 2:
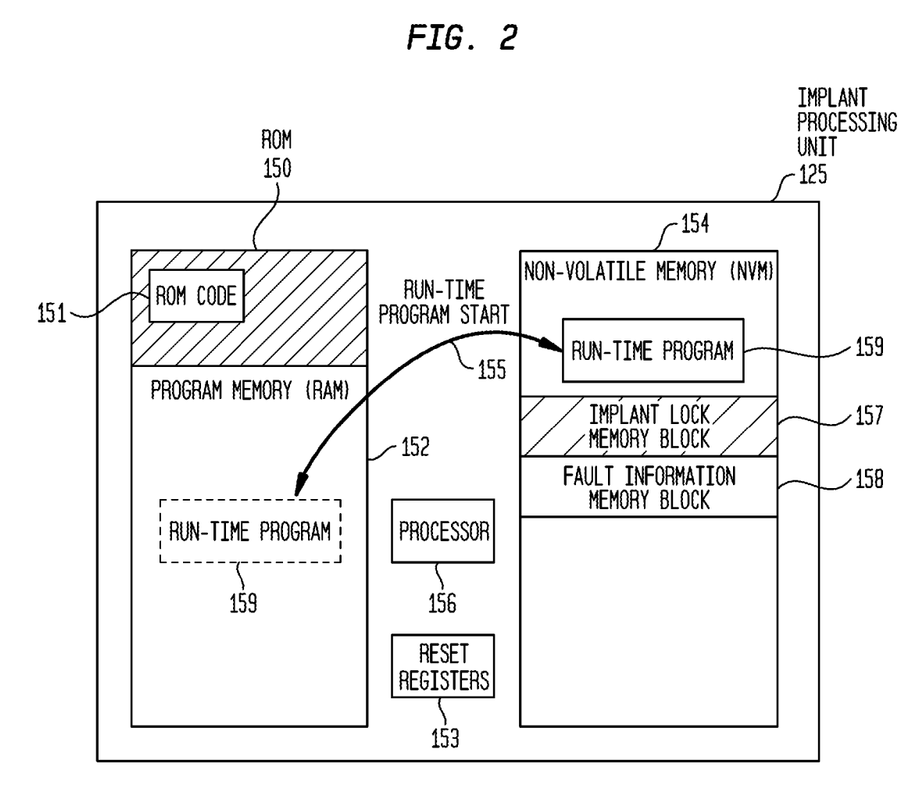
FIG. 2 is a schematic block diagram of a processing unit, in accordance with certain embodiments presented herein.
Figure 3:
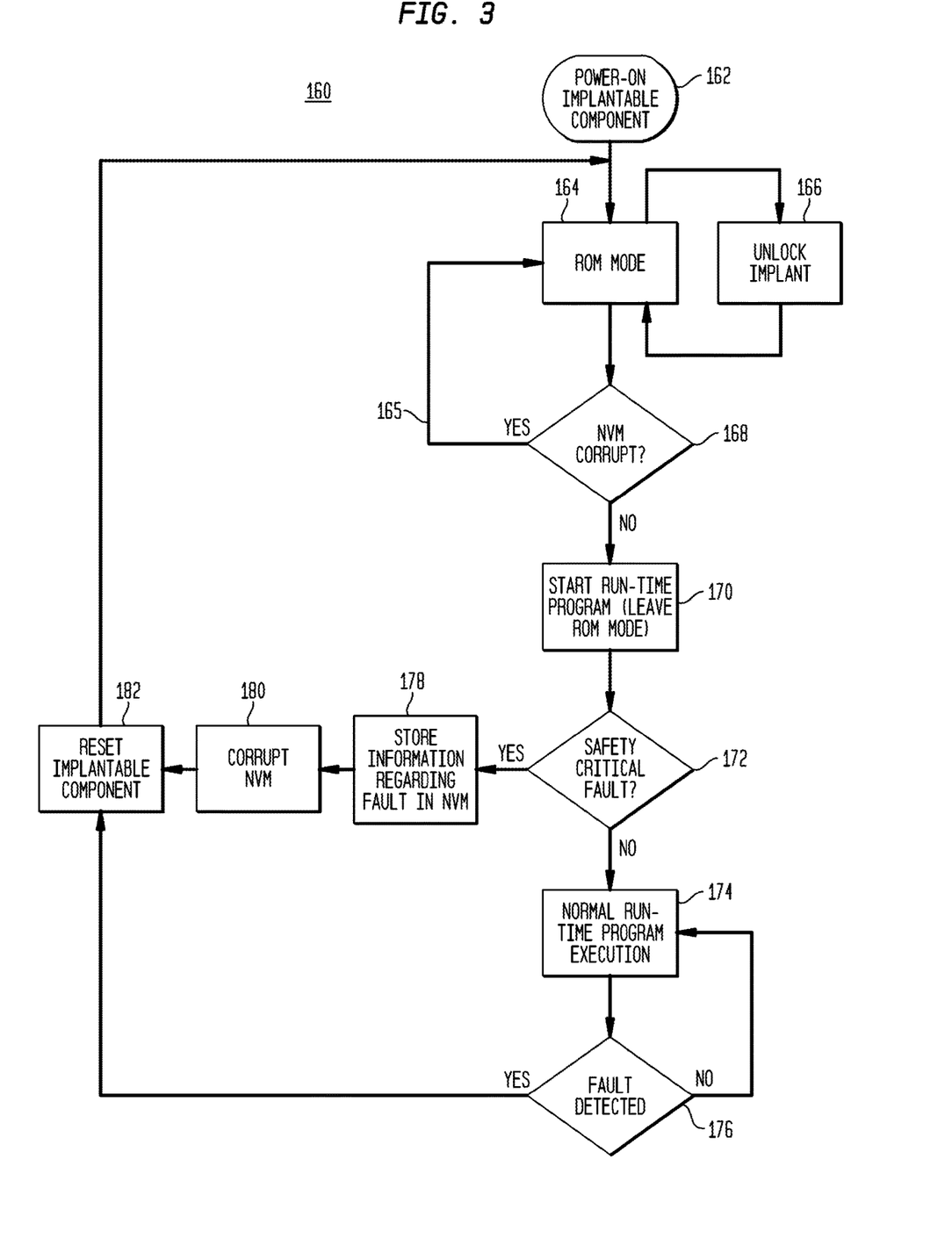
FIG. 3 is a detailed flowchart of a method, in accordance with certain embodiments presented herein.

More specifically, FIG. 2 is a functional diagram illustrating one embodiment of the implant processing unit 125 of FIG. 1, while FIG. 3 is a detailed flowchart illustrating a method 160 for operation of the implant processing unit 125 in accordance with certain embodiments herein.

Referring first to FIG. 2, the implant processing unit 125 comprises read-only memory (ROM) 150, program memory/random access memory (RAM) 152, non-volatile memory (NVM) 154, and at least one processor (e.g., microprocessor, microcontroller, etc.) 156. The ROM 150 includes code 151, sometimes referred to herein as ROM code or boot code (e.g., hardwired into the ASIC). The NVM 154 includes a run-time program 159, an implant lock memory block 157, and a fault information memory block 158.

Referring next to FIG. 3, the method 160 starts at 162 where the implantable component 104 is started or restarted (i.e., powered-up/on). The implantable component 104 may be powered-up, for example, in response to a command received from the sound processing unit 112 or another external device (e.g., in response to a button press at the external device, in response to a detected presence/proximity of the external device to the implantable component, etc.). At 164, in response to the implantable component 104 being powered-on, the ROM code 151 in the ROM 150 is executed by the at least one processor 156. Execution of the ROM code 151 by the at least one processor 156 is sometimes referred to herein as a "ROM Mode" of the implantable component 156.

The ROM code 151, when executed by the at least one processor 156, is configured to, among other operations, perform a validation of the NVM 154. That is, at 168, the ROM code 151 is configured to determine whether the NVM is valid or corrupt (e.g., includes any corrupt memory blocks). For example, the ROM code 151 may be configured to perform a Cyclic Redundancy Check (CRC) check on the NVM 154.

If, at 168, the ROM code 151 determines that the NVM 154 is invalid/corrupt (i.e., includes one or more corrupt memory blocks), then, as shown by arrow 165, the implantable component 104 will remain in the ROM mode indefinitely. This is described further below.

If, at 168, the ROM code 151 is able to successfully validate the NVM 154, then at 170 the run-time program 159 is loaded from NVM 154 into program memory 152 and executed by the at least one processor 156. This is shown in FIG. 2 by arrow 155.

As used herein, the run-time program 159 refers to a collection of code, instructions, etc. that, when executed by the at least one processor 156, enable the implantable component 104 to perform its intended operational functions. In the specific case of implantable component 104, these intended operational functions include, among other operations, receiving stimulation commands from the sound processing unit 112 and delivering electrical stimulation signals to the recipient via electrodes 126. Therefore, if the NVM 154 is not corrupt, the implantable component 104 exits the ROM mode and enters a "run-time mode" or "run-time state."

When the run-time program 159 is loaded and first executed by the at least one processor 156, at 172 a determination is made as to whether or not the implantable component 104 was powered-up due to a reset responsive to a safety critical fault. This determination may be made by examining temporary reset registers 153. These temporary reset registers 152 are part of, or used by, the diagnostic safety mechanisms (running as part of the run-time program 159) to immediately store information associated with a detected fault. These temporary reset registers 153 are not reset/erased in response to a reset of the implantable component. As such, these temporary reset registers 153 can be interrogated by the run-time program 159 at 172 to determine the cause of the fault and, accordingly, the cause of the reset. However, these temporary reset registers 153 cannot be read by external devices and are continually updated with various information such any information stored therein will be flushed out within a certain period of time.

This determination is made by the initial/preliminary code (i.e., the first few code lines) of the run-time program 159 and, as such, is one of the first operations performed by the implantable component in the run-time mode. More particularly, this determination can be made before the recipient is exposed to any potentially hazardous conditions, such as before delivering stimulation to the recipient. Additionally, this determination can be made before the battery is connected, before battery voltage or current measurements are performed and before the microphone is enabled.

In the situation in which the implantable component 104 is powered-on normally (e.g., in response to instructions/commands received from sound processing unit 112), then the implantable component 104 determines that the restart (or start in the very first instance) was not due to a reset and method proceeds to 174. Additionally, in certain situations, the implantable component 104 may determine that the implantable component is powered-on following a reset, but that the reset was due to a so-called "uncategorized fault" or a "non-safety critical fault," determined from the temporary reset registers 153. Again, in this case, the method proceeds to 174 (i.e., a fault of unknown origin).

At 174, the implantable component 104 operates in the run-time mode (i.e., provides the full functionality of the implantable component) until a fault is detected at 176 or the implantable component is powered-down via a normal process (not shown in FIG. 3). If a fault is detected at 176, then the implantable component 182 is substantially immediately reset at 182 so as to place the implantable component in a safe state where any potential hazards/dangers to the recipient are remediated. Further details regarding fault detection are described further below.

As noted above, the reset of implantable component at 182 substantially immediately follows the detection of the fault at 176. In particular, at this stage, no information regarding the fault is stored in the fault information memory block 158 (i.e., the suffered fault is an uncategorized fault). One reason that the reset of implantable component at 182 substantially immediately follows the detection of the fault at 176 is to avoid any unnecessary processing at that time when the implantable component is potentially in an unsafe state.

After the implantable component is reset, method 160 returns to 164. That is, the reset causes the implantable component to restart in the ROM mode. As noted, when in the ROM mode, the implantable component 104 is configured to determine whether the NVM is valid or corrupt (e.g., perform a CRC check on the NVM 154). At this point, since the fault that caused the last reset is an uncategorized fault, no operations have been performed by the implantable component 104 to alter the validity of the NVM 154. As such, method proceeds to 170 where the run-time program 159 is loaded from NVM 154 into program memory 152 and executed by the at least one processor 156. Again, this is shown in FIG. 2 by arrow 155.

As noted above, when the run-time program 159 is loaded and first executed by the at least one processor 156, at 172 a determination is made as to whether or not the implantable component 104 was powered-up due to a reset responsive to a safety critical fault. This determination may again be made by examining the temporary reset registers 153.

As noted, the determination at 172 is made by the initial/preliminary code (i.e., the first few code lines) of the run-time program 159 and, as such, is one of the first operations performed by the implantable component in the run-time mode (i.e., before the recipient is exposed to any potentially hazardous conditions, such as before delivering stimulation to the recipient).

If, at 172, the implantable component 102 was reset due to a non-safety critical fault, then, at 174, the implantable component 104 operates in the run-time mode until another fault is detected at 176 or the implantable component is powered-down via a normal process. However, if it is determined at 172 that the fault suffered by the implantable component 104 is a safety critical fault, then at 178 the implantable component 104 stores information regarding the fault (e.g., information regarding the reason, cause, and/or type of the fault) in the fault information memory block 158 of the NVM 154. Additionally, at 180, the implantable component 104 purposely corrupts the implant lock memory block 157. That is, the implant lock memory block 157 is a dedicated memory block added into the NVM 154 for the purpose of being corrupted when a safety critical fault of the implantable component 104 is detected. As described further below, corrupting the implant lock memory block 157 in the NVM 154 renders the NVM 154 corrupt/invalid.

After the cause of the information regarding the fault has been stored in the fault information memory block 158 (at 178) and the implant lock memory block 157 has been corrupted (at 180), then the implantable component 182 is reset at 182. One reason that the operations of 178 and 180 can be performed at this time is that the safety critical fault 172 is detected at the beginning of the run-time mode (i.e., before full functionality is enabled). As such, the additional processing at this does not result in risk to the recipient.

After the implantable component is reset at 180, method 160 again returns to 164 (i.e., the implantable component again restarts in the ROM mode). As noted, when in the ROM mode, the implantable component 104 is configured to determine, at 168, whether the NVM 154 is valid or corrupt (e.g., perform a CRC check on the NVM 154). At this point, since the fault that caused the last reset was previously determined to be a safety critical fault, the implantable component 104 performed operations at 180 to purposely corrupt implant lock memory block 157. Therefore, in this situation, the ROM code 151 determines at 168 that the NVM 154 is invalid/corrupt (i.e., includes a corrupt implant lock memory block 157). Therefore, as shown by arrow 165, the implantable component 104 will remain in the ROM mode indefinitely The implantable component 104 will remain in the ROM mode until the implantable component 104 is affirmatively unlocked, at 166. The implantable component 104 may be unlocked, for example, via commands received from an external device, such as a computing device or fitting system used by a clinician. Stated differently, if the NVM 154 is corrupt (i.e., one or more memory blocks included therein are corrupt), the implantable component 104 will not, and cannot, exit the ROM mode without the receipt of commands from an external device. The retention of the implantable component 104 in the ROM mode is sometimes referred to herein as a "locked mode" or "locked state" for the implantable component 104. When the implantable component 104 is in this locked mode, the implantable component can only perform limited functions. These limited functions may include: only allowing limited read and write functions to the NVM 154 of the implantable component 104 from a secondary device (i.e., enable interrogation of the implantable component allowing a clinician or other individual to determine what kind of condition caused the lock), allowing a clinician or other individual to unlock the implant, and allowing a clinician or other individual to reprogram the NVM 154 with new firmware.

Figure 4:
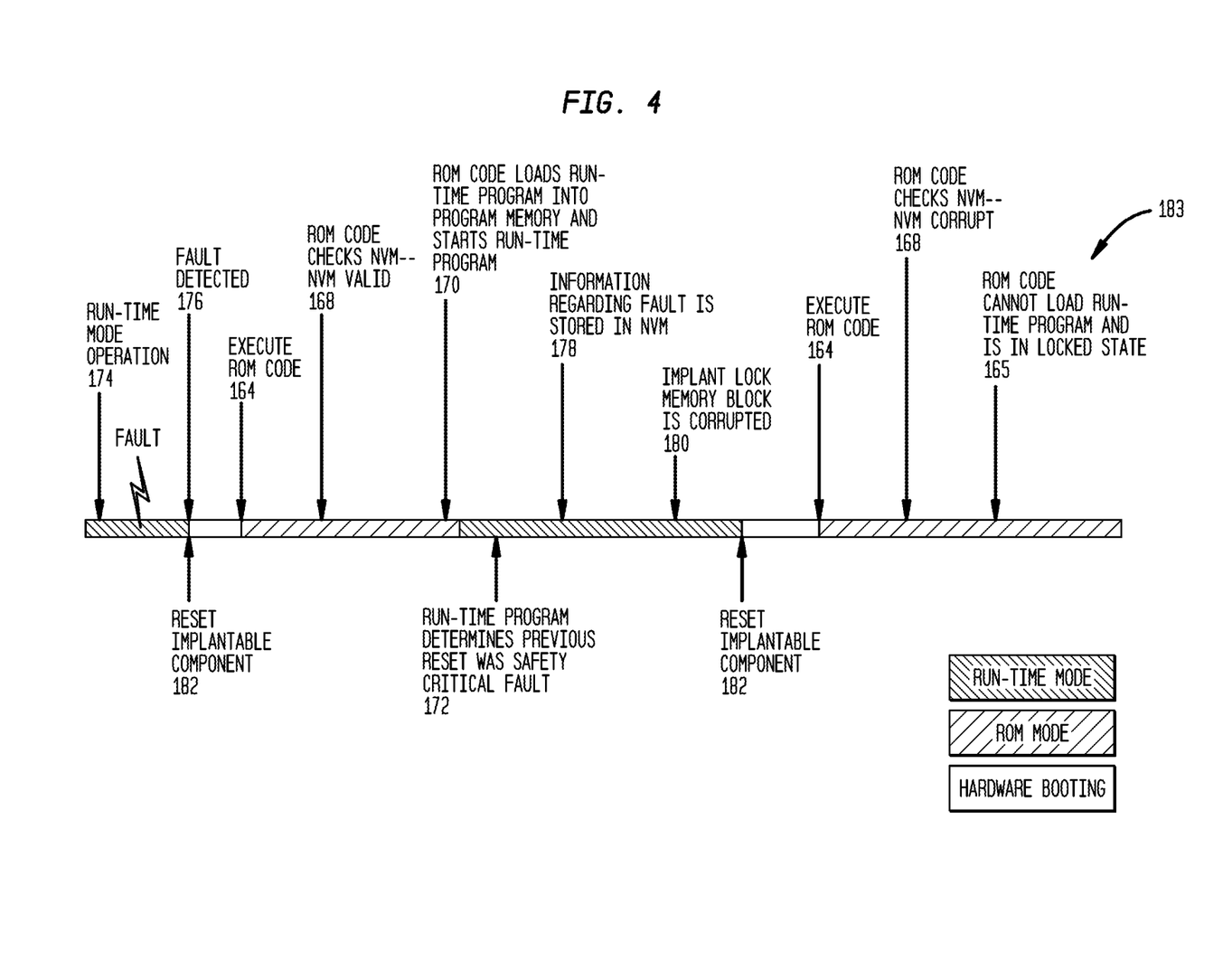
FIG. 4 is a timeline illustrating an order of certain operations performed in the method of FIG. 3, in accordance with certain embodiments presented herein.

FIG. 4 is a unit-less timeline 183 illustrating the order of the operations performed in the above example of FIG. 3. The timeline 183 of FIG. 4 starts at 174, where the implantable component 104 is operating in the run-time mode normally (i.e., not subsequent to a fault-triggered reset).

As noted above, the implantable component 104 is electronically locked when a safety critical fault is detected so as to ensure that the implantable component will not, and cannot, continue to operate with this fault. The electronic locking mechanism described herein can, for example, prevent more serious consequences to develop due to the fault and ensure that the recipient visits a clinic where the condition that caused the lock can be properly assessed, and a decision can be made as to the future use of the implant. As noted above, safety critical faults are faults that have the potential to cause harm to an individual using the device (i.e., in the case of implantable components, the recipient).

As noted above, devices configured to implement the techniques presented herein, such as implantable component 104, are also configured to implement one or more diagnostic safety mechanisms that are active while an individual is using the device. These diagnostic safety mechanisms are configured to detect the occurrence of faults and when appropriate, store information about these faults. In the specific case of an implantable component, one example of a safety critical faults that could be detected by these diagnostic safety mechanisms may be a short circuit condition at the implant electronics and/or an implanted electrode array (e.g., determined by checking the battery discharge current). Another example of a safety critical fault that could be detected by these diagnostic safety mechanisms is a condition in which the voltage of an implanted battery has reached or exceeded a maximum battery voltage threshold (e.g., determined by directly measuring the battery voltage and/or measuring the battery charging current). Another example of a safety critical fault that could be detected by these diagnostic safety mechanisms is a condition in which an implanted battery has been overcharged (i.e., a battery overcharge condition, determined by measuring the battery voltage and/or measuring the battery charging current).

Another example of a safety critical fault that could be detected by these diagnostic safety mechanisms is a condition in which there is an error with a voltage measurement system of the implantable component (e.g., determined by checking if a voltage can be measured that cannot exist within the system). A still other example of a safety critical fault that could be detected by these diagnostic safety mechanisms is a condition in which there is electrical leakage to tissue of the recipient (e.g., determined by checking if electrodes in tissue are pulled towards an uncontrolled potential). Another example of a safety critical fault that could be detected by these diagnostic safety mechanisms is a condition in which memory of the implantable component has experienced a hard fault/error (e.g., determined by periodical reading back blocks of program memory after it has been loaded from NVM and performing a CRC on the read back blocks of program memory). It is to be appreciated that the safety critical faults described above are illustrative of the types of safety critical faults and does not represent an exhaustive list of safety critical faults that could be detected in accordance with embodiments presented herein. Indeed, different devices may have altogether different types of faults that could be deemed to be safety critical so as to lead to an electronically locked device.

Embodiments presented herein have primarily been described with reference to cochlear implant and FIGS. 1-4, in particular, have generally been described with reference to one example arrangement of a cochlear implant configured to implement the techniques presented. However, as noted elsewhere wherein, the techniques presented herein may also or alternatively be used with other types of cochlear implants and other types of electronic devices that can suffer safety critical faults, such as implantable components of medical prostheses that provide a wide range of therapeutic benefits to recipients. For example, it is to be appreciated that the techniques presented herein may be used with auditory prostheses other than cochlear implants, including acoustic hearing aids, auditory brainstem stimulators, bone conduction devices, middle ear auditory prostheses, direct acoustic stimulators, bimodal auditory prosthesis, bilateral auditory prosthesis, etc., as well as other implantable components, such as implantable pacemakers, spinal cord stimulators, deep brain stimulators, motor cortex stimulators, sacral nerve stimulators, pudendal nerve stimulators, vagus/vagal nerve stimulators, trigeminal nerve stimulators, retinal or other visual prosthesis/stimulators, occipital cortex implants, diaphragm (phrenic) pacers, pain relief stimulators, other neural or neuromuscular stimulators, etc.

Figure 5:
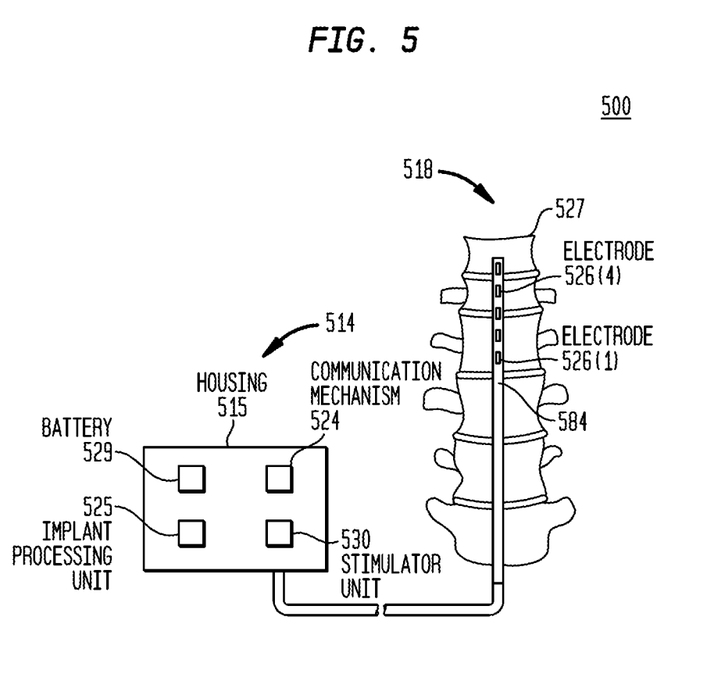
FIG. 5 is a schematic block diagram illustrating a spinal cord stimulator, in accordance with certain embodiments presented herein.

For example, FIG. 5 is a simplified schematic diagram illustrating a spinal cord stimulator 500 in which certain embodiments presented herein may be implemented.

More specifically, the spinal cord stimulator 500 comprises an implant body (main module) 514 and a stimulating assembly 518 implanted under the skin/tissue (tissue) of the recipient. The implant body 514 generally comprises a hermetically-sealed housing 515 in which an implant processing unit 525, a battery 529, and a stimulator unit 530 are disposed. The implant body 514 also includes a communication mechanism 524 for communicating within an external device. The communication mechanism 524 may comprise, for example, a wireless transceiver, an internal/implantable coil and RF interface circuitry, etc.

The stimulating assembly 518 is implanted in a recipient adjacent/proximate to the recipient's spinal cord 527 and comprises five (5) stimulation electrodes 526, referred to as stimulation electrodes 526(1)-526(5). The stimulation electrodes 526(1)-526(5) are disposed in an electrically-insulating body 584 and are electrically connected to the stimulator 530 via conductors (not shown) that extend through the electrically-insulating body 584.

Following implantation, the implant processing unit 525 is configured to generate stimulation signals for delivery to the spinal cord 527 via stimulation electrodes 526(1)-526(5). Although not shown in FIG. 5, an external controller may also be provided to transmit signals through the recipient's skin/tissue to the implant processing unit 525 for control of the stimulation signals.

Similar to the embodiments described above, the implant processing unit 525 is configured to implement one or more diagnostic safety mechanisms that are active while a recipient is using the implantable component. These diagnostic safety mechanisms can be configured to, for example, monitor for short circuit conditions at the implant electronics and/or the electrode array 528, monitor the battery 529 (e.g., monitoring to determine whether a maximum battery voltage threshold has been reached/exceeded, monitoring for a battery overcharge condition, etc.), monitor for faults in a voltage measurement system, monitor for electrical leakage to tissue, monitoring for memory hard errors, etc.

In accordance with certain embodiments presented herein, when these diagnostic safety mechanisms of implant processing unit 525 detect a fault in the operation of the spinal cord stimulator 500, the implant processing unit 125 is configured to execute a reset of the spinal cord stimulator 500 to ensure the spinal cord stimulator immediately ceases operation and is placed in a safe state (i.e., a state in which any potential hazards/dangers to the recipient are remediated). The reset of the spinal cord stimulator 500 could be achieved in a number of different manners. In one example, the reset disconnects all electrodes from tissue, stops/terminates all processing, and disconnects the internal battery 529 from the other internal circuitry (thereby powering down the implant if no external power is supplied).

Following the reset, the implant processing unit 525 restarts operation and determines the cause of the reset. If the implant processing unit 525 determines that the cause of the reset was a "safety critical fault" (i.e., a fault/condition causing a potentially hazardous situation for the recipient), then the implant processing unit 525 is configured to initiate another reset and cause the implantable component to enter an electronic "locked mode," where only basic, non-hazardous functionality is supported. This functionality may include, for example, allowing interrogation of internal memory of the implantable component and the ability to unlock the implantable component. The unlocking may only be allowed, for example, in a clinic following an assessment by a trained clinician or engineer as to the risk associated with the fault that triggered the safety check. Further details regarding electronically locking of an implantable component, such as spinal cord stimulator 500, have been described further below with reference to FIGS. 2 and 3. In other words, the implant processing unit 525 may be configured to operate similarly to implant processing unit 125 described above with reference to FIGS. 2 and 3.

Figure 6:
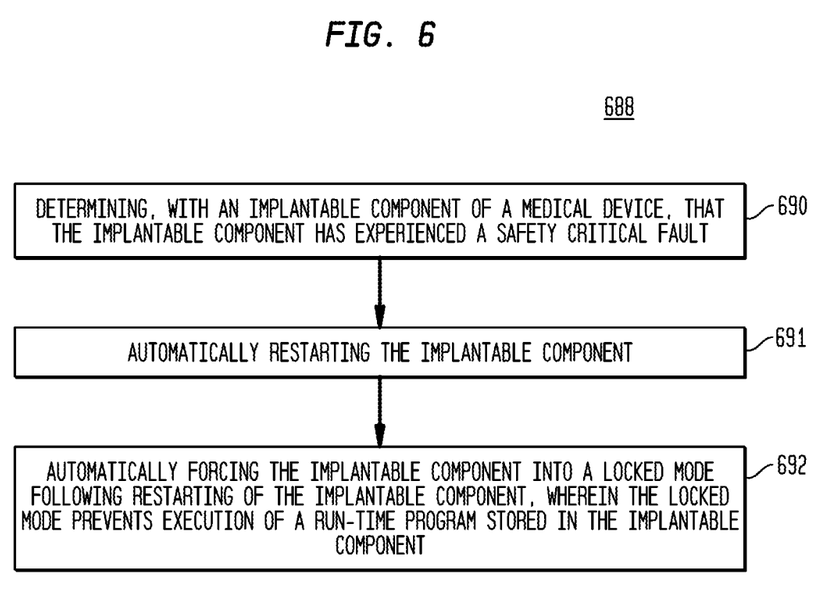
FIG. 6 is a flowchart of a method, in accordance with certain embodiments presented herein.

FIG. 6 is a flowchart of a method 690 in accordance with embodiments presented herein. Method 690 begins at 691 where an implantable component of a medical device determines that the implantable component has experienced a safety critical fault. At 692, the implantable component automatically restarts the implantable component. At 694, the implantable component is forced into a locked mode following restarting of the implantable component, wherein the locked mode prevents execution of a run-time program stored in the implantable component.

As detailed above, presented herein are techniques for implementing an electronic "lock mode" within an electronic device, such as in implantable medical components (implantable components). In particular, the techniques presented herein configure an implantable component such that if a fault of a serious nature is detected (i.e., a safety critical fault), then the implantable component ceases normal operation immediately, and diverts to the locked mode, with minimal operation (e.g., potentially including disconnecting all electrodes from tissue, stopping all processing and disconnecting the internal battery from the internal circuitry). The recipient can then, for example, proceed to a clinic to have the issue diagnosed.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
    determining, with an implantable component of a medical device, that the implantable component has experienced a safety critical fault, wherein the implantable component includes read-only memory (ROM) and non-volatile memory (NVM);
    in response to determining that the medical device has experienced the safety critical fault, purposely corrupting, by the implantable component, a memory block of the non-volatile memory (NVM); and
    automatically forcing the implantable component into a locked mode,
    wherein the locked mode prevents execution of a run-time program stored in the implantable component.

2. The method of claim 1, wherein the locked mode only allows limited read and write functions to memory of the implantable component from a secondary device.

3. The method of claim 1, wherein automatically forcing the implantable component into the locked mode comprises:
    automatically restarting the implantable component such that the implantable component executes code stored in read-only memory (ROM) of the implantable component, wherein execution of the code stored in the ROM checks non-volatile memory (NVM) of the implantable component for corrupt memory blocks;
    determining that a memory block in the NVM is corrupt; and
    in response to determining that the memory block in the NVM is corrupt, indefinitely executing the code stored in the ROM.

4. The method of claim 3, wherein determining that the memory block in the NVM is corrupt comprises:
    performing a Cyclic Redundancy Check (CRC) check on the NVM.

5. The method of claim 1, wherein prior to determining that the implantable component has experienced the safety critical fault, the method comprises:
    determining that the implantable component has experienced an uncategorized fault;
    restarting the implantable component such that the implantable component executes code stored in read-only memory (ROM) of the implantable component, wherein execution of the code stored in the ROM checks non-volatile memory (NVM) of the implantable component for corrupt memory blocks;
    executing the code stored in the ROM without detecting any corrupt memory blocks;
    loading, into program memory, the run-time program for execution; and
    upon execution of the run-time program, determining that the uncategorized fault is a safety critical fault.

6. The method of claim 5, wherein in response to determining that the uncategorized fault is a safety critical fault, the method comprises:
    storing an indication of the safety critical fault in the NVM.

7. The method of claim 1, wherein detecting a safety critical fault comprises:
    detecting a short circuit condition in the implantable component.

8. The method of claim 1, wherein the implantable component includes an implantable battery, and wherein detecting a safety critical fault comprises:
    detecting that a voltage of the implantable battery has reached a maximum voltage threshold or detecting that the implantable battery has been overcharged.

9. An implantable medical device, comprising:
    non-volatile memory (NVM) configured to store a run-time program; and
    at least one processor configured to:
        execute the run-time program, wherein the execution of the run-time program detects a safety critical fault in operation of the implantable medical device;
        in response to the detection of the safety critical fault, purposely corrupt, by the implantable medical device, a memory block of the NVM;
        restart the implantable medical device and initiate a locked mode, wherein the locked mode includes validation of the NVM of the implantable medical device;
        determine that the NVM is corrupt; and
        in response to determination that the NVM is corrupt, prevent re-execution of the run-time program.

10. The implantable medical device of claim 9, wherein the locked mode only allows limited read and write functions to the NVM from a secondary device.

11. The implantable medical device of claim 9, wherein to validate the NVM of the device, the processor is configured to perform a Cyclic Redundancy Check (CRC) check on the NVM.

12. The implantable medical device of claim 9, wherein prior to the determining that the medical device has experienced the safety critical fault, the processor is configured to:
    determine that the medical device has experienced an uncategorized fault;
    in response to determining that the medical device has experienced the uncategorized fault, restart the medical device and execute code stored in read-only memory (ROM) of the medical device;
    validate the NVM;
    upon successfully validating the NVM, loading into program memory the run-time program for execution; and upon execution of the run-time program, determining that the uncategorized fault is a safety critical fault.

13. The implantable medical device of claim 12, wherein in response to determining that the uncategorized fault is a safety critical fault, the processor is configured to:
store an indication of the safety critical fault in the NVM.

14. The implantable medical device of claim 9, wherein to prevent re-execution of the run-time program, the processor continually executes code stored in read-only memory (ROM) of the implantable medical device.

15. The implantable medical device of claim 9, wherein the NVM and the at least one processor are configured to be implanted in a recipient of the implantable medical device.

16. One or more non-transitory computer readable storage media encoded with instructions that, when executed by a processor of an implantable medical device, cause the processor to:
determine, using data from an integrated diagnostic mechanism of the implantable medical device, that the implantable medical device has experienced a safety critical fault, wherein the implantable medical device comprises non-volatile memory (NVM) and read-only memory (ROM);
in response to determining that the implantable medical device has experienced the safety critical fault, purposely corrupt, by the implantable medical device, a memory block of the non-volatile memory (NVM);
automatically restart the implantable medical device;
determine whether non-volatile memory (NVM) of the implantable medical device is corrupt; and
in response to determining that the NVM is corrupt, indefinitely execute code stored in read-only memory (ROM) of the implantable medical device.

17. The one or more non-transitory computer readable storage media of claim 16, wherein the instructions that cause the processor to indefinitely execute code stored in the ROM of the implantable medical device comprise instructions that cause the processor to:
prevent execution of a run-time program stored in NVM of the implantable medical device.

18. The one or more non-transitory computer readable storage media of claim 16, wherein the instructions that cause the processor to indefinitely execute code stored in the ROM of the implantable medical device comprise instructions that cause the processor to:
only allow limited read and write functions to the NVM of the implantable medical device from a secondary device.

19. The one or more non-transitory computer readable storage media of claim 16, wherein the instructions that cause the processor to determine whether the NVM of the implantable medical device is corrupt comprise instructions that cause the processor to:
perform a Cyclic Redundancy Check (CRC) check on the NVM.

20. The one or more non-transitory computer readable storage media of claim 16, further comprising instructions that, prior to determining that the implantable medical device has experienced the safety critical fault cause the processor to:
determine that the implantable medical device has experienced an uncategorized fault;
in response to determining that the implantable medical device has experienced the uncategorized fault, restart the implantable medical device in a mode in which the processor executes the code stored in the ROM, wherein the code stored in the ROM checks the NVM for corrupt memory blocks;
execute the code stored in the ROM without detecting any corrupt memory blocks;
load, into program memory, a run-time program for execution; and
upon execution of the run-time program, determine that the uncategorized fault is a safety critical fault.

21. The one or more non-transitory computer readable storage media of claim 20, further comprising instructions that, in response to determining that the uncategorized fault is a safety critical fault cause the processor to:
store an indication of the safety critical fault in the NVM.

22. The one or more non-transitory computer readable storage media of claim 16, wherein the instructions that cause the processor to determine that the implantable medical device has experienced a safety critical fault comprise instructions that cause the processor to:
detect a short circuit condition in the implantable medical device.

23. The one or more non-transitory computer readable storage media of claim 16, wherein the implantable medical device comprises an implantable component that includes an implantable battery, and wherein the instructions that cause the processor to determine that the implantable medical device has experienced a safety critical fault comprise instructions that cause the processor to:
detect that a voltage of the implantable battery has reached a maximum voltage threshold or detect that the implantable battery has been overcharged.

* * * * *